(12) United States Patent
Davenport et al.

(10) Patent No.: US 8,535,384 B2
(45) Date of Patent: Sep. 17, 2013

(54) ACETABULAR SCREW HOLE COVERS WITH POROUS COATING

(75) Inventors: Austen Davenport, Columbia City, IN (US); W. Jason Slone, Silver Lake, IN (US); Margaret Kelly, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 57 days.

(21) Appl. No.: 13/206,626

(22) Filed: Aug. 10, 2011

(65) Prior Publication Data
US 2013/0041474 A1   Feb. 14, 2013

(51) Int. Cl.
*A61F 2/34* (2006.01)

(52) U.S. Cl.
USPC ............................ 623/22.34; 623/22.35

(58) Field of Classification Search
USPC .......... 623/22.21, 22.34, 22.35, 22.36, 22.37
See application file for complete search history.

(56) References Cited

U.S. PATENT DOCUMENTS

| | | | |
|---|---|---|---|
| 4,542,539 A * | 9/1985 | Rowe et al. | 623/23.57 |
| 4,955,325 A | 9/1990 | Zarnowski et al. | |
| 5,370,702 A | 12/1994 | Jones | |
| 5,571,198 A | 11/1996 | Drucker et al. | |
| 5,609,648 A | 3/1997 | Oehy et al. | |
| 5,645,606 A | 7/1997 | Oehy et al. | |
| 5,782,929 A | 7/1998 | Sederholm | |
| 5,876,456 A | 3/1999 | Sederholm et al. | |
| 5,888,205 A | 3/1999 | Pratt et al. | |
| 5,911,758 A | 6/1999 | Oehy et al. | |
| 5,925,077 A | 7/1999 | Williamson et al. | |
| 6,120,546 A | 9/2000 | Dye et al. | |
| 6,152,962 A | 11/2000 | DeCarlo, Jr. | |
| 6,709,462 B2 | 3/2004 | Hanssen | |
| 7,842,094 B2 | 11/2010 | Le Bon et al. | |
| 2003/0163203 A1 | 8/2003 | Nycz et al. | |
| 2008/0255672 A1 | 10/2008 | Gil | |
| 2010/0057217 A1 | 3/2010 | Breimesser et al. | |
| 2010/0256771 A1 | 10/2010 | Roberts et al. | |

FOREIGN PATENT DOCUMENTS

| | | |
|---|---|---|
| EP | 0900552 A1 | 3/1999 |
| FR | 2838329 A1 | 10/2003 |
| WO | WO-9515734 A1 | 6/1995 |

OTHER PUBLICATIONS

"Exceed ABT™ Acetabular System Product Rationale," brochure. Biomet Europe (2010) 27 sheets.
"RingLoc® + Acetabular System," brochure. (Jan. 31, 2010) 48 pages.

* cited by examiner

*Primary Examiner* — David Isabella
*Assistant Examiner* — Randy Shay
(74) *Attorney, Agent, or Firm* — Harness, Dickey

(57) ABSTRACT

An acetabular shell can include a substrate and a screw hole cover. The substrate can define a screw hole configured to receive a screw to fix the substrate to bone. The screw hole cover is formed separate from the substrate and attached to the substrate to cover the screw hole, and configured to be ruptured.

24 Claims, 2 Drawing Sheets

ACETABULAR SCREW HOLE COVERS WITH POROUS COATING

FIELD

The present disclosure relates to covers for screw holes in an acetabular shell.

BACKGROUND

This section provides background information related to the present disclosure which is not necessarily prior art.

Prosthetic implants used in total hip replacements can include an acetabular shell and a femoral component, with an articular interface therebetween. The acetabular shell is placed in an acetabulum and can define screw holes through which screws can be inserted to fix the acetabular shell to a pelvic bone. Some of the screw holes may be used while others of the screw holes may not be used.

SUMMARY

This section provides a general summary of the disclosure, and is not a comprehensive disclosure of its full scope or all of its features.

An acetabular shell can include a substrate and a screw hole cover. The substrate can define a screw hole configured to receive a screw to fix the substrate to bone. A screw hole cover can be separate from the substrate, attached to the substrate to cover the screw hole, and configured to be ruptured.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DESCRIPTION OF VARIOUS EMBODIMENTS

Example embodiments will now be described more fully with reference to the accompanying drawings.

Figure 1:
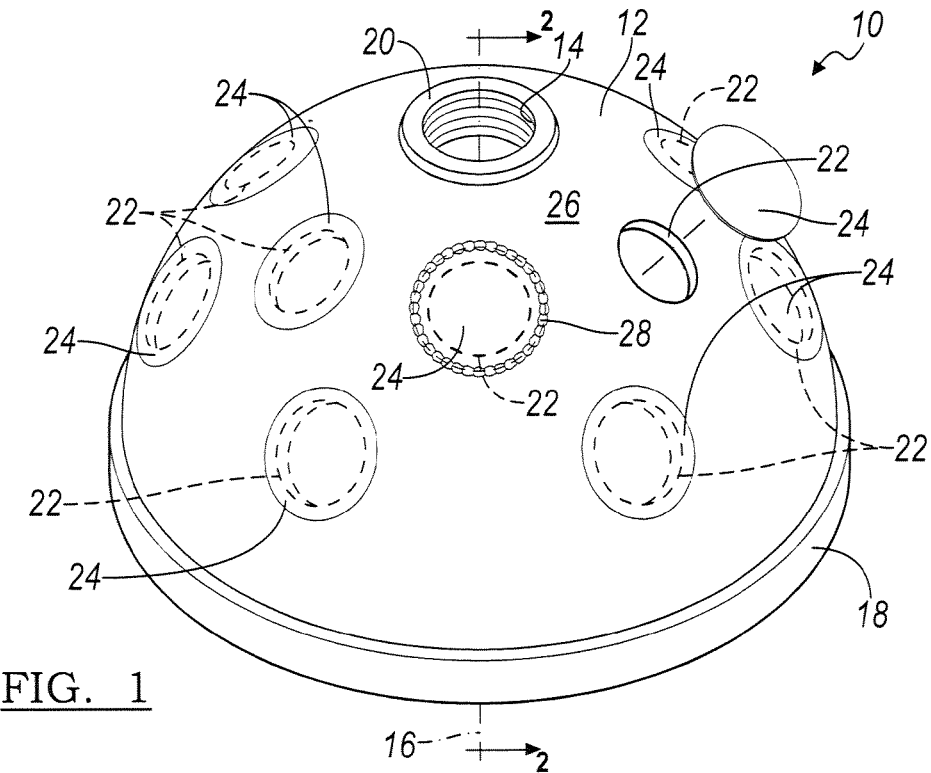
FIG. 1 is a perspective view of an acetabular shell including a screw hole cover according to the principles of the present disclosure.
Figure 4:
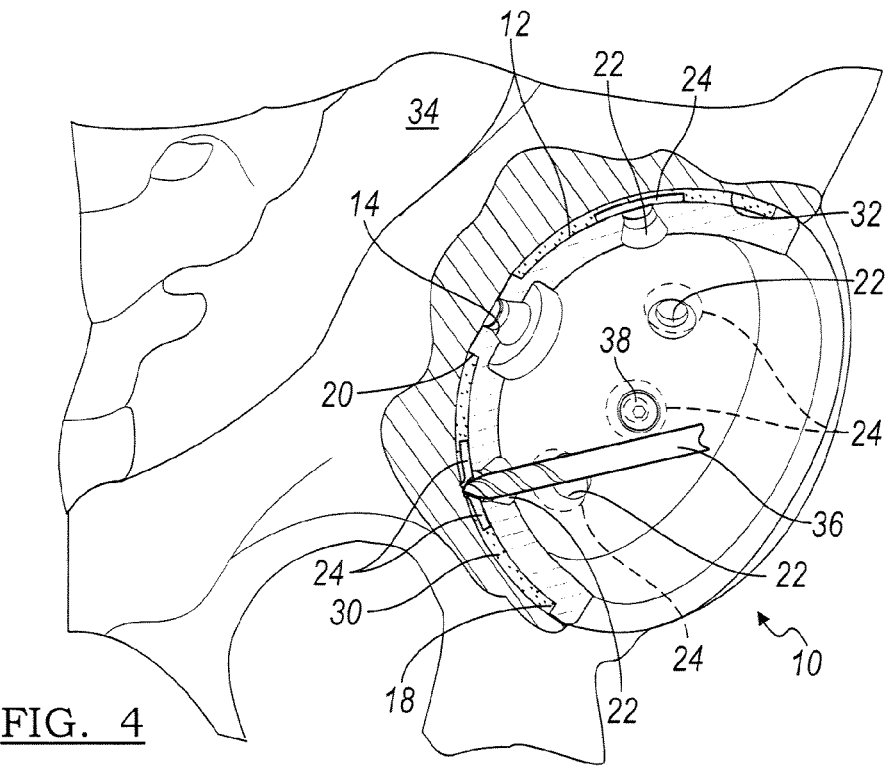
FIG. 4 is an environmental view with a partial section view illustrating uses of an acetabular shell according to the principles of the present disclosure.

Referring to FIG. 1, an acetabular shell 10 can include a curved wall or substrate 12. The substrate 12 can be made from polymer, metal, metal alloys, and/or composites (e.g., ceramics). The substrate 12 can define a center hole 14 extending through the substrate 12 along a center axis 16 of the substrate 12. The center hole 14 can be used to position the acetabular shell 10 within an acetabulum (FIG. 4). The substrate 12 can include a shoulder 18 extending around the perimeter of the substrate 12 and a shoulder 20 extending around the center hole 14. The shoulders 18, 20 can extend beyond a surface of the substrate 12.

The substrate 12 can also define one or more screw holes 22, which can be disposed at various locations on the substrate 12. The screw holes 22 can extend through the substrate 12. The screw holes 22 are configured to receive screws to fix the acetabular shell 10 to bone. For example, the screw holes 22 can be threaded, counterbored, and/or countersunk.

The acetabular shell 10 can also include one or more screw hole covers 24 that are formed separate from, and then attached to, the substrate 12. In an embodiment, the screw hole covers 24 are fixed to the outer surface 26 of the substrate 12 to cover the screw holes 22 to at least prevent debris from migrating through the screw holes 22. To this end, the screw hole covers 24 can be disks and can be sized to cover the screw holes 22.

The screw hole covers 24 can be configured to be ruptured (e.g. drilled through, punctured) and/or to withstand application of a treatment such as surface roughening or working (e.g., blasting, abrading, sanding). Surface working may be done to prepare the substrate 12 and the screw hole covers 24 for application of a coating that promotes bony ingrowth or bony ongrowth. The coating may be a porous coating and/or a plasma spray. Alternatively, the coating may not be applied, which reduces manufacturing costs, and surface working may be done to promote bone growth directly onto or into the substrate 12 and the screw hole covers 24. The ability to be ruptured and/or to withstand surface working can be achieved through the selection of a material and a thickness of the screw hole covers 24.

The screw hole covers 24 can be formed (e.g. cut, stamped, machined) from a source sheet of material, such as metal (e.g., titanium, tantalum, cobalt, cobalt-chromium-molybdenum, stainless steel) foil. The screw hole covers 24 can be connected to the outer surface 26 of the substrate 12 to form a watertight seal to prevent debris from migrating through the screw holes 22. The screw hole covers 24 can have a thickness of about 0.001 inches (0.0254 millimeters) to about 0.080 inches (2.032 millimeters), inclusive; further including about 0.005 inches (0.127 millimeters) to about 0.015 inches (0.381 millimeters), and further including about 0.010 inches (0.254 millimeters). The specific thickness and the specific material of the screw hole covers 24 can be interdependent. For example, where a first material is stronger than a second material, the screw hole covers 24 can have a first thickness for the first material and the screw hole covers 24 can have a second thickness for the second material that is greater than the first thickness.

The screw hole covers 24 can be attached to the substrate 12 using a weld 28, such as a laser weld, which can extend around the perimeter of the screw hole covers 24. Although only one of the screw hole covers 24 is shown welded to the substrate 12, each of the screw hole covers 24 can be welded to the substrate 12. In various embodiments, the screw hole covers 24 can be attached to the substrate 12 using an adhesive. The screw hole covers 24 can be bonded directly to the substrate 12 without using a filler material between the screw hole covers 24 and the substrate 12. Alternatively or additionally, other welding and bonding techniques (e.g., using an electrical current) may be used.

Figure 2:
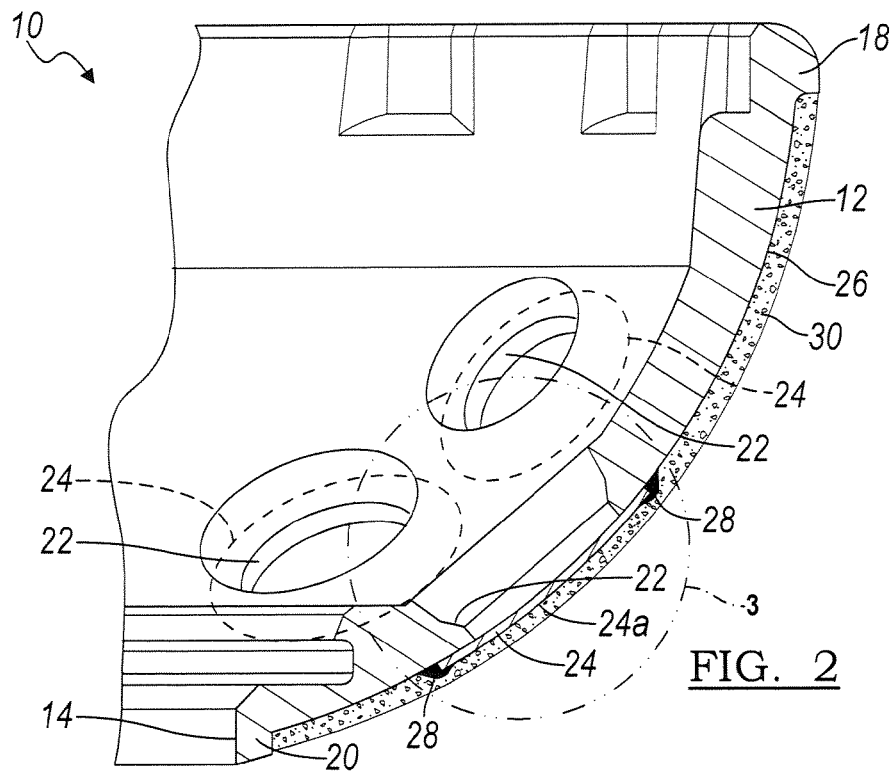
FIG. 2 is a section view of the acetabular shell of FIG. 1 taken along line 2-2, the acetabular shell including a porous coating applied to an outer surface of a substrate according to the principles of the present disclosure.

Referring to FIG. 2, the acetabular shell 10 can also include a porous coating 30 applied to the outer surface 26 of the substrate 12 and/or to outer surfaces 24a of the screw hole covers 24. As conventionally known, the porous coating 30 allows bony ingrowth/ongrowth and fixation at the acetabular shell 10. The bond between the porous coating 30 and the surrounding bone can be strengthened as bone grows onto or into the porous coating 30. Inserting screws into the screw holes 22 provides even more fixation, especially prior to significant bony ingrowth/ongrowth or where bone loss is great or bony ingrowth/ongrowth is unlikely.

The porous coating 30 can be applied to the substrate 12 and to the screw hole cover 24 after the screw hole cover 24 is attached to the substrate 12. Before the porous coating 30 is applied, the outer surface 26 of the substrate 12 and the outer surfaces 24a of the screw hole covers 24 can be worked to prepare the outer surfaces 24a, 26 for the application of the porous coating 30. Alternatively, the porous coating 30 may not be applied to the substrate 12, and the screw hole covers 24, and the outer surfaces 24a, 26 can be worked to promote bone growth directly on the substrate 12 and the screw hole covers 24. As indicated above, the thickness of the screw hole cover 24 can be sufficient to withstand such surface working.

The porous coating 30 can cover the outer surface 26 of the substrate 12 and/or the screw hole covers 24. The porous coating 30 can extend from the shoulder 18 around the outer perimeter of the substrate 12 to the shoulder 20 around the center hole 14 in the substrate 12. The thickness of the porous coating 30 can be less than or equal to the distance by which the shoulder 18 and/or the shoulder 20 project from the outer surface 26. The thickness of the porous coating 30 may be established as the porous coating 30 is applied so that no machining is required to achieve a desired thickness.

Figure 3:
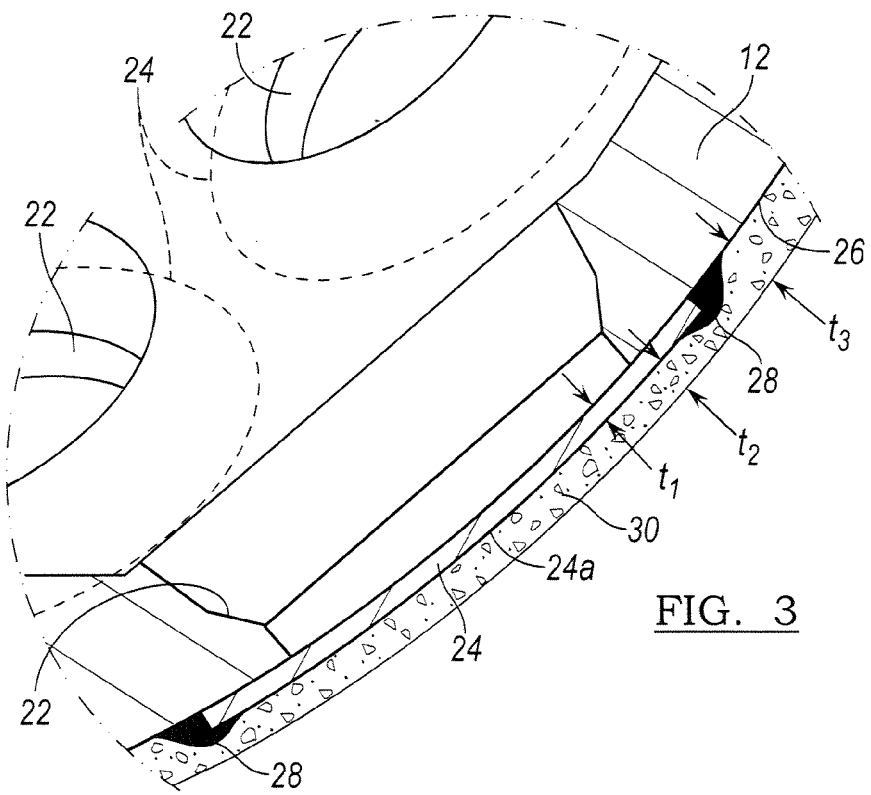
FIG. 3 is an enlarged view of a portion of FIG. 2 within circle 3-3.

Referring to FIG. 3, the porous coating 30 can be thinner where the porous coating 30 is applied to the screw hole covers 24 to account for the thickness of the screw hole covers 24. For example, the screw hole covers 24 can have a first thickness $t_1$ and the porous coating 30 can have a second thickness $t_2$ where the porous coating 30 is applied to the screw hole covers 24. The porous coating 30 can also have the third thickness $t_3$ where the porous coating 30 is applied directly to the substrate 12. The third thickness $t_3$ can be equal to the sum of the first thickness $t_1$ and the second thickness $t_2$. The second thickness $t_2$ of the coating 30, however, is substantially formed so that the first and second thicknesses $t_1$ and $t_2$ are substantially equal to the third thickness $t_3$. The porous coating 30 need not be thinned to allow use of the screw holes 22, as described herein.

Referring to FIG. 4, fixation of the acetabular shell 10 within an acetabulum 32 of a pelvic bone 34 is illustrated. A surgeon may select a subset of the screw holes 22 to use and use a drill bit 36 to drill holes through the screw hole covers 24 covering the screw holes 22 in the subset. The surgeon may drill the holes before the acetabular shell 10 is fixed to the pelvic bone 34, although FIG. 4 illustrates drilling once the acetabular shell 10 is placed. The surgeon may insert a screw 38 through the screw holes 22 and the screw hole covers 24 that are drilled. The rest of the screw holes 22 (i.e., those undrilled) remain covered by the screw hole covers 24.

An acetabular shell according to the principles of the present disclosure allows a surgeon to not have to insert screw hole plugs into screw holes that are not used to prevent debris from migrating through the unused screw holes. Further, the porous coating can be applied to the outer surface of the substrate and to the screw hole covers at the same time, and the screw holes do not need to be plugged before, or chipped around after, the porous coating is applied. Additionally, the screw hole covers 24 may be attached and the outer surfaces 24a thereof, as well as the outer surface 26, may be prepped according to conventional porous coating techniques without special consideration.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. An acetabular shell prosthesis, comprising:
 a substrate having an inner surface and an outer surface defining a screw hole through the inner surface and the outer surface, the screw hole being configured to receive a screw to fix the substrate to bone within an acetabulum;
 a screw hole cover that is formed separate from the substrate and attached to the substrate to cover the screw hole; and
 a porous coating applied to the outer surface of the substrate and to the screw hole cover,
 wherein the screw hole cover has a first thickness, the porous coating has a second thickness where the porous coating is applied to the screw hole cover, the porous coating has a third thickness where the porous coating is applied to the substrate, and the third thickness is equal to a sum of the first thickness and the second thickness.

2. The acetabular shell prosthesis of claim 1, wherein ruptured includes the screw hole cover being configured to be drilled through.

3. The acetabular shell prosthesis of claim 1, wherein the screw hole cover is attached to the outer surface of the substrate.

4. The acetabular shell prosthesis of claim 3, wherein the screw hole cover is welded to the outer surface of the substrate.

5. The acetabular shell prosthesis of claim 1, wherein the screw hole cover is made from titanium.

6. The acetabular shell prosthesis of claim 1, wherein the screw hole cover has a thickness of about 0.001 inches to about 0.080 inches, inclusive.

7. The acetabular shell prosthesis of claim 1, wherein the screw hole cover forms a watertight seal to prevent debris from migrating through the screw hole.

8. The acetabular shell prosthesis of claim 1, wherein the screw hole cover and the outer surface of the substrate are configured to withstand surface working.

9. The acetabular shell prosthesis of claim 1, wherein:
 said screw hole cover comprises
 a metal foil disk that is formed separate from the curved wall, attached to the outer surface of the curved wall to cover the screw hole, configured to withstand surface working, and configured to be ruptured.

10. The acetabular shell prosthesis of claim 9, wherein:
 the metal foil disk is cut from a titanium foil source of a selected thickness and separate from the curved wall; and
 the metal foil disk has a thickness less than a thickness of the curved wall.

11. The acetabular shell prosthesis of claim 10, wherein the metal foil disk is attached to the outer surface of the curved wall by laser welding to the outer surface of the curved wall.

12. The acetabular shell prosthesis of claim 10, wherein the metal foil disk is attached to the outer surface of the curved wall using an adhesive.

13. The acetabular shell prosthesis of claim 10, wherein the metal foil disk has a thickness of about 0.005 inches to about 0.010 inches, inclusive.

14. The acetabular shell prosthesis of claim 10, wherein the attachment at the metal foil disk forms a watertight seal to prevent debris from migrating through the screw hole.

15. The acetabular shell prosthesis of claim 9, wherein the porous coating extends continuously over the outer surface of the curved wall and the metal foil disk.

16. A method for making an acetabular shell prosthesis, comprising:

forming a substrate including a screw hole extending through the substrate;

forming a screw hole cover to have a first thickness from a source material separate from the substrate;

attaching the screw hole cover to the substrate to cover the screw hole; and applying a porous coating directly to an outer surface of the substrate and to the screw hole cover after attaching the screw hole cover to the substrate so that the porous coating has a second thickness at the screw hole cover and the porous coating has a third thickness at the substrate, wherein the third thickness is substantially equal to a sum of the first thickness and the second thickness.

17. The method of claim 16, wherein attaching the screw hole cover includes attaching the screw hole cover to the outer surface of the substrate.

18. The method of claim 17, wherein attaching the screw hole cover includes laser welding the screw hole cover to the outer surface of the substrate.

19. The method of claim 17, wherein attaching the screw hole cover includes attaching the screw hole cover to the outer surface of the substrate using an adhesive.

20. The method of claim 16, further comprising selecting the source material to be a metal foil.

21. The method of claim 20, wherein selecting the source material to be a metal foil includes selecting a titanium foil.

22. The method of claim 16, wherein the source material has a thickness of about 0.001 inches to about 0.080 inches, inclusive.

23. The method of claim 16, wherein attaching the screw hole cover includes forming a watertight seal between the substrate and the screw hole cover to prevent debris from migrating through the screw hole.

24. The method of claim 16, further comprising working the outer surface of the substrate and an outer surface of the attached screw hole cover before applying the porous coating to the outer surface of the substrate and to the screw hole cover.

\* \* \* \* \*

UNITED STATES PATENT AND TRADEMARK OFFICE
CERTIFICATE OF CORRECTION

| | | |
|---|---|---|
| PATENT NO. | : 8,535,384 B2 | Page 1 of 1 |
| APPLICATION NO. | : 13/206626 | |
| DATED | : September 17, 2013 | |
| INVENTOR(S) | : Austen Davenport | |

It is certified that error appears in the above-identified patent and that said Letters Patent is hereby corrected as shown below:

In the Specification

Column 2, Line 42, Delete "inclusive;" and insert --inclusive,--.

In the Claim

Column 4, Line 51, In Claim 9, after "comprises", insert --:--.

Signed and Sealed this
Twenty-ninth Day of April, 2014

Michelle K. Lee
*Deputy Director of the United States Patent and Trademark Office*